(12) United States Patent
Corder (10) Patent No.: US 10,285,970 B2
(45) Date of Patent: May 14, 2019

(54) METHOD OF TREATING ENDOTHELIAL DYSFUNCTION WITH OENOTHEIN B AND PROANTHOCYANIDINS

(71) Applicant: Nugerontix Limited, Stoke-on-Trent (GB)

(72) Inventor: Roger Corder, Heathfield (GB)

(73) Assignee: Nugerontix Limited (GB)

( * ) Notice: Subject to any disclaimer, the term of this patent is extended or adjusted under 35 U.S.C. 154(b) by 0 days.

(21) Appl. No.: 15/328,706

(22) PCT Filed: Jul. 24, 2015

(86) PCT No.: PCT/GB2015/052148
§ 371 (c)(1),
(2) Date: Jan. 24, 2017

(87) PCT Pub. No.: WO2016/012806
PCT Pub. Date: Jan. 28, 2016

(65) Prior Publication Data
US 2017/0216245 A1    Aug. 3, 2017

(30) Foreign Application Priority Data

Jul. 25, 2014 (GB) .................................. 1413228.6

(51) Int. Cl.
| | | |
|---|---|---|
| *A61K 31/353* | (2006.01) | |
| *A61K 9/00* | (2006.01) | |
| *A61K 31/198* | (2006.01) | |
| *A61K 31/7048* | (2006.01) | |
| *A23L 33/105* | (2016.01) | |
| *A23L 2/52* | (2006.01) | |
| *A61K 9/50* | (2006.01) | |
| *A61K 36/73* | (2006.01) | |
| *A61K 36/87* | (2006.01) | |

(52) U.S. Cl.
CPC .............. *A61K 31/353* (2013.01); *A23L 2/52* (2013.01); *A23L 33/105* (2016.08); *A61K 9/00* (2013.01); *A61K 9/0095* (2013.01); *A61K 9/50* (2013.01); *A61K 31/198* (2013.01); *A61K 31/7048* (2013.01); *A61K 36/73* (2013.01); *A61K 36/87* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 2013/0164394 A1* | 6/2013 | Ferrari | ................. | A61K 31/198 424/765 |
| 2014/0010871 A1 | 1/2014 | Mackler | | |
| 2014/0018415 A1* | 1/2014 | Rinsch | ................. | A61K 45/06 514/455 |

FOREIGN PATENT DOCUMENTS

| | | | |
|---|---|---|---|
| GB | 2497899 | A | 6/2013 |
| JP | 2004091390 | A | 3/2004 |
| JP | 2011037720 | A | 2/2011 |
| WO | 2009128738 | A2 | 10/2009 |
| WO | 2013186680 | A1 | 12/2013 |
| WO | WO 2013/186680 | * | 12/2013 |

OTHER PUBLICATIONS

Caton, P. et al. Regulation of Vascular Endothelial Function by Procyanidin Rich Foods and Beverages. J of Agricultural and Food Chemistry 58(7)4008-4013, 2010. (Year: 2010).*
Corder, R. Red Wine, Chocolate and Vascular Health. Heart 94(7)821-823, Jul. 2008. (Year: 2008).*
Kiss, A. et al. Polyphenolic Compounds Characterization and Reactive Nitrogen Species Scavenging Capacity of Oenothera paradoxa Defatted Seed Extracts. Food Chemistry 131(2)485-492, 2012. (Year: 2012).*
Gupta H. et al. A Randomized, Double Blind, Placebo Controlled Trial to Evaluate Efficacy and Tolerability of an Optimized Botanical Combination . . . Phytotherapy Research 26:265-272, 2012. (Year: 2012).*
Booth et al, Berry Polyphenols Inhibit Digestive Enzymes: a Source of Potential Health Benefits?, Food Digestion (2012), vol. 3, p. 1-7.
Vilahur et al, Supplementation with a pomegranate extract abrogates hypercholesterolemia-induced coronary endothelial dysfunction in swine, European Heart Journal (2013), p. 141.
Corder et al, The procyanidin-induced pseudo laminar shear stress response: a new concept for the reversal of endothelial dysfunction, Clinical Science (2004), vol. 107, p. 513-517.
Caton et al, Regulation of Vascular Endothelial Function by Procyanidin-Rich Foods and Beverages, Journal of Agricultural and Food Chemistry (2010), vol. 58, p. 4008-4013.
Roquim et al, Jaboticaba (*Myrciaria jaboticaba* (Vell.) Berg), a Brazilian grape-like fruit, improves plasma lipid profile in streptozotocin-mediated oxidative stress in diabetic rats, Food Research International (2013) vol. 54, No. 1, p. 650-659.
Kiss et al, Novel Biological Properties of Oenthera paradoxa Defatted Seed Extracts: Effects on Metallopeptidase Activity, Journal of Agricultural and Food Chemistry (2008) vol. 56, No. 17, p. 7845-7852.
McDougall et al, Towards fruitful metabolomics: High throughput analysis of polyphenol composition in berries using direct infusion mass spectrometry, Journal of Chromatography B (2008) vol. 871, No. 2, p. 362-369.
Burton-Freeman et al, Strawberry Modulates LDL Oxidation and Postprandial Lipemia in Response to Hight-Fat Meal in Overweight Hyperlipidemic Men and Women, Journal of the American College of Nutrition (2010), vol. 29, No. 1, p. 46-54.

(Continued)

*Primary Examiner* — Ralph J Gitomer
(74) *Attorney, Agent, or Firm* — IpHorgan Ltd.

(57) ABSTRACT

The present application concerns compositions comprising ellagitannins and proanthocyanidins, and the use of such compositions for preventing or treating endothelial dysfunction. The compositions of the invention comprise at least one ellagitannin in combination with at least one proanthocyanidin. The present application also concerns methods of treating, preventing, or delaying the onset of endothelial dysfunction using compositions comprising ellagitannins and proanthocyanidins.

13 Claims, 4 Drawing Sheets

(56) References Cited

OTHER PUBLICATIONS

Romero et al, Therapeutic Use of Citrulline in Cardiovascular Disease, Cardiovascular Drug Reviews (2006), vol. 24, No. 3-4, p. 275-290.
Gu et al, Nutrient Requirements Concentrations of Proanthocyanidins in Common Foods and Estimations of Normal Consumption, The Journal of Nutrition (2004), p. 613-617.
United Kingdom Intellectual Property Office, "Search Report" issued in UK application No. GB1413228.6, dated Apr. 21, 2015.
European Patent Office acting as the International Searching Authority, "International Search Report" and "Written opinion" issued in international application No. PCT/GB2015/052148, dated Dec. 8, 2015.
United Kingdom Intellectual Property Office, "Examination Report" issued in UK application No. GB1703061.0, dated Oct. 18, 2018.

* cited by examiner

METHOD OF TREATING ENDOTHELIAL DYSFUNCTION WITH OENOTHEIN B AND PROANTHOCYANIDINS

The present application concerns polyphenol compositions, and the use of such compositions in preventing or treating endothelial dysfunction.

BACKGROUND

Polyphenol compounds are a class of organic compounds characterized by the presence of multiple phenol structural units. Thousands of naturally occurring polyphenol compounds are known, and the broad class of polyphenol compounds can be broken down into subgroups, such as flavonoids, which contain a 15 carbon atom scaffold comprising two aromatic rings linked by a three carbon bridge. The sub-class flavonoids can be broken down further to include compounds such as procyanidins, which are oligomeric compounds formed primarily from catechin and epicatechin molecules. One important class of non-flavonoid polyphenols are phenolic acids such as gallic acid, a precursor of hydrolysable tannins, such as ellagitannins.

Natural sources of polyphenols include common foodstuffs such as tea, coffee, cocoa, red wine, beer, cider, fruits, vegetables and nuts (*Journal of Agricultural and Food Chemistry*, 2010, 58: 4959-69). Other sources of polyphenols include plants that are generally not regarded as foodstuffs, but may be used as traditional herbal medicines, such as flowering plants of the *Epilobium* genus, commonly known as willowherb.

The endothelium is a single layer of cells lining every blood vessel. Maintaining healthy endothelial function is critical for overall health and wellbeing. Endothelial dysfunction is a common characteristic of altered cardiovascular function leading to coronary heart disease, and more generally atherothrombotic diseases including stroke and peripheral vascular disease. All risk factors for cardiovascular disease—raised LDL cholesterol, diabetes, smoking, high blood pressure (hypertension), increasing age and lack of exercise—have been linked to endothelial dysfunction. Endothelial dysfunction is widely recognised as a precursor to atherosclerotic lesion formation. Common characteristics of endothelial dysfunction include: increased inflammation; reductions in the healthy anti-thrombotic functions of the endothelium; increased synthesis of mediators that stimulate remodelling and vascular stiffness; and increased vasoconstriction with reduced vasodilatation.

Endothelial dysfunction is not only associated with the underlying mechanisms leading to cardiovascular disease, but also as a risk factor for cardiovascular events, including myocardial infarction. The severity of endothelial dysfunction is closely associated with increased risk of mortality in patients with chronic heart failure. Although statins and angiotensin-converting enzyme inhibitors cause modest improvements in endothelial function, there are currently no pharmaceutical medications that specifically treat endothelial dysfunction.

Nitric oxide (NO) plays a crucial role in normal endothelial function, including maintaining vascular homeostasis, modulation of vasodilator tone, regulation of local cell growth, and protection of the vessel from injurious consequences of platelets and cells circulating in blood. NO is continuously synthesized in endothelial cells by the enzyme nitric oxide synthase (eNOS). However, in patients with endothelial dysfunction, NO production can be impaired and endothelial dysfunction is often observed experimentally and clinically as reduced NO-dependent vasodilatation.

eNOS synthesizes nitric oxide using the amino acid L-arginine in the presence of the co-factor tetrahydrobiopterin (BH4). Recent approaches to the treatment of endothelial dysfunction have used both BH4 and L-arginine supplements in an attempt to boost production of NO. However, both of these approaches have drawbacks and lack reproducibility. In particular, BH4 readily oxidises to an inactive form, making it difficult to calculate how much of a given dose of BH4 is actually bioavailable to a patient in need thereof (*Antioxidants and Redox Signaling*, 2014, 20: 3040-77). The importance of BH4 has been further documented by overexpression of eNOS in mouse models, in which it was found that the resultant BH4—eNOS imbalance led to augmented formation of atherosclerotic lesions (*Journal of Clinical Investigation*, 2002, 110: 331-40). Moreover, the use of L-arginine supplements has been linked to higher post-infarction mortality, likely as a consequence of endothelial BH4 deficiency (*Journal of the American Medical Association*, 2006, 295: 58-64).

A further characteristic of endothelial dysfunction is increased synthesis of the vasoconstrictor peptide endothelin-1. Antagonists of endothelin-1 cause vasodilation and improve endothelium-dependent vasodilator responses in older people (*Clinical Science*, 2011, 120: 485-9), and in patients with atherosclerosis (*Circulation*, 2010, 122: 958-66).

Research on reversing endothelial dysfunction has identified the transcription factor Kruppel-like factor 2 (KLF2) as a key regulator of healthy endothelium, which affords protection from atherosclerosis. It has been proposed that agents that increase KLF2 in the endothelium could be used to treat endothelial dysfunction (*Cardiovascular Pathology*, 2013; 22:9-15). Some procyanidins are known to increase KLF2 transiently for a few hours (*Journal of Agricultural & Food Chemistry*, 2010; 58:4008-4013). Identification of agents that could sustain this induction would have greater therapeutic utility in restoring or maintaining endothelial function.

The effects of dietary polyphenols on vascular function have been investigated for more than 50 years. Hawthorn berry extract has been used for centuries as a treatment for cardiovascular disease including chronic heart failure (*Journal of Clinical Pharmacology*, 2002, 42: 605-12). The beneficial effects on cardiac function have been attributed to the high content of flavanols, principally procyanidins. High flavanol cocoa drinks and high flavanol dark chocolate have been found to improve endothelial function in patients with chronic heart failure, coronary artery disease, and diabetes (*European Heart Journal*, 2012, 33: 2172-80; *Journal of the American College of Cardiology*, 2008, 51: 2141-9; *Journal of the American College of Cardiology*, 2010, 56: 218-24). Grape seed extract, which is also mainly composed of procyanidins, also lowers blood pressure (*Metabolism Clinical and Experimental*, 2009, 58: 1743-6) and improves vascular function (*Journal of Biomedicine and Biotechnology*, 2004, 5: 272-8). The improvement in cardiovascular function with products containing high amounts of procyanidins is consistent with studies on isolated vessels showing that purified procyanidins cause endothelium-dependent vasodilatation via NO release (U.S. Pat. No. 6,706,756 B1), and inhibit the synthesis of endothelin-1 (*Journal of Agricultural and Food Chemistry*, 2010, 58: 4008-13).

The anti-atherosclerotic actions of pomegranate juice (*Punica Granatum*) have been reported (U.S. Pat. No. 8,221,806 B2). Pomegranate juice and pomegranate fruit extract promote endothelium-dependent vasodilatation of isolated vessels (*Nitric Oxide*, 2007, 17: 50-4). The components responsible for these effects have not been described.

Previous human volunteer and patient studies specifically focusing on dietary polyphenols and their impact on endothelial dysfunction have been poorly executed. Studies that have claimed to investigate such compounds and their effects on cardiovascular health have used complex, poorly defined mixtures of compounds, such that it was impossible to attribute any overall health benefit to any one particular component. Moreover, many studies have only measured indirect effects, such as blood pressure, rather than looking at nitric oxide production or endothelin-1 synthesis. For example, Basu et al. investigated the effect on cardiovascular health of berries (*Nutrition Reviews* 2010, 68: 168-177), while Asgary et al. investigated the effects of pomegranate juice on blood pressure (*ARYA Atherosclerosis*, 2013, 9: 326-31). However, both berries and pomegranate juice contain a wide variety of compounds, including not only polyphenol compounds such as proanthocyanidins or ellagitannins but also other substances known to have health benefits such as vitamins, minerals and fibre. Thus, it is impossible to draw any clear conclusions from these studies regarding the effects of dietary polyphenols on nitric oxide production and endothelial dysfunction.

There is a need in the art for new treatments for endothelial dysfunction. In particular, it would be advantageous to provide new treatments for endothelial dysfunction comprising an optimised mixture of purified polyphenol compounds, since it is anticipated that the side-effect profile from such compositions would be favourable. Compounds that improve endothelial function are also expected to be useful ergogenic aids. Thus, the provision of new ergogenic compositions is a further aim of the present invention.

SUMMARY OF THE INVENTION

In a first embodiment, the invention concerns compositions comprising, or consisting essentially of, at least one ellagitannin in combination with at least one proanthocyanidin, preferably wherein said at least one proanthocyanidin is at least one procyanidin.

In a further embodiment, the invention concerns compositions comprising:
at least one ellagitannin;
at least one proanthocyanidin, preferably wherein said at least one proanthocyanidin is at least one procyanidin;
citrulline or a citrulline salt; and
aspartic acid or an aspartate.

In a further embodiment, the present invention is directed to a composition consisting essentially of:
at least one ellagitannin;
at least one proanthocyanidin, preferably wherein said at least one proanthocyanidin is at least one procyanidin;
citrulline or a citrulline salt; and
aspartic acid or an aspartate.

In a further embodiment, the present invention is directed to a composition consisting of:
at least one ellagitannin;
at least one proanthocyanidin, preferably wherein said at least one proanthocyanidin is at least one procyanidin;
citrulline or a citrulline salt; and
aspartic acid or an aspartate.

In a further embodiment, the present invention is directed to a pharmaceutical composition comprising a composition of the invention as defined above together with at least one pharmaceutically acceptable excipient or carrier.

In a further embodiment, the present invention is directed to a pharmaceutical composition comprising a composition of the invention as defined above, wherein the composition is pharmaceutically acceptable and is in unit dosage form. Preferably, wherein the unit dosage form is selected from tablets, capsules, buccal tablets, orally disintegrating tablets, oral fast dissolving tablets, dispersible tablet, masticatory, granules, dry suspension, injection, solution, slow-release formulation, controlled-release formulation and rapid-release formulation.

In a further embodiment, the present invention is directed to a composition of the invention where the ellagitannin and proanthocyanidin are microencapsulated.

In a further embodiment, the invention concerns compositions of the invention for use in preventing or treating diseases associated with endothelial dysfunction including arteriosclerosis, hypertension, pulmonary hypertension, coronary artery disease, chronic heart failure, peripheral artery disease, diabetes, chronic renal failure and erectile dysfunction.

In a further embodiment, the invention concerns the use of compositions of the invention as ergogenic aids.

In a further embodiment, processes for preparing the compositions of the invention are presented.

DEFINITIONS

One Dalton as used herein is equivalent to one unified atomic mass unit (u). It is a standard unit that is used for indicating atomic mass, and is an accepted non-SI unit. One Dalton is approximately the mass of one proton/neutron. Thus, the mass of hydrogen is one Dalton, since hydrogen only contains a single proton and no neutrons.

Within the context of the present invention, the word "about" in relation to a numerical value or range of values is intended to refer to plus or minus ten percent of that value (±10%). Thus "about 90" should be construed as a range spanning the values 81-99.

Certain features which are, for clarity, described herein in the context of separate embodiments, may be combined in any manner. Conversely, various features that are, for brevity, described in the context of a single preferred feature, may also be provided separately or in any sub-combination. Further, references to values stated in ranges include each and every value within that range.

Note that one or more further activities may be performed in addition to those described.

DETAILED DESCRIPTION

The present invention is based on the unexpected discovery that administering at least one ellagitannin with at least one proanthocyanidin causes a surprising improvement in endothelial function, e.g. greater than might be expected based on the properties of these polyphenol molecules alone. Thus, in a first embodiment, the invention is directed towards compositions comprising as active ingredient at least one proanthocyanidin and at least one ellagitannin, preferably wherein said at least one proanthocyanidin is a procyanidin.

Proanthocyanidins are a class of oligomeric polyphenol compounds composed primarily of (+)-catechin and (−)-epicatechin molecules, as shown below:

(+)-catechin (-)-epicatechin

Proanthocyanidins can occur as polymers of up to 50 monomer units.

Procyanidins are a class of proanthocyanidin that consist exclusively of epicatechin and catechin molecules (*Natural Products Report* 2009, 26:1001-1043).

Structural elucidation of proanthocyanidins, such as procyanidins, is far from trivial, and requires complex NMR analysis, usually at low temperature. However, it is known that catechin/epicatechin units can be linked through a single carbon-carbon bond: a C4-C8 or a C4-C6 linkage. Alternatively, an additional ether bond can be present, i.e. C4-C6, C2-O—C7 or C4-C8, C2-O—C7. The figure below shows one example of a procyanidin tetramer, joined via C4-C8 linkages:

In the compositions described herein, the at least one proanthocyanidin is preferably one or more procyanidins.

In one embodiment, the procyanidins used in the compositions of the present invention are enriched in the size range of trimer to hexamer. In other words, the procyanidins used in the compositions of the present invention contain an increased amount of procyanidin trimers, procyanidin tetramers, procyanidin pentamers and procyanidin hexamers, relative to the amounts of other oligomers of procyanidin.

In one embodiment, the proanthocyanidins used in the compositions of the present invention are enriched in the size range of trimer to hexamer and are galloylated. Preferably, the proanthocyanidins used in the compositions of the present invention are procyanidins, are enriched in the size range of trimer to hexamer and are galloylated.

The term "galloylated" is intended to mean that at least one gallic acid molecule is attached to the proanthocyanidin molecule. The gallic acid molecule(s) can be attached in any position. However, it is commonly found that the at least one gallic acid molecule is joined to the (epi)catechin core via an ester linkage to the hydroxyl group at the 3 position. Galloylated proanthocyanidins are frequently found when the proanthocyanidins are derived from particular plant sources, including grapes and grape products. An example of a galloylated epicatechin molecule is shown below:

In one embodiment, the proanthocyanidins used in the compositions of the present invention have a molecular weight range of about 800 to about 1900 Daltons. Preferably, the proanthocyanidins used in the compositions of the present invention are procyanidins and have a molecular weight range of about 800 to about 1900 Daltons.

In another embodiment, the proanthocyanidins used in the compositions of the present invention have a molecular weight range of about 900 to about 1800 Daltons or a molecular weight range of about 1150 to about 1750 Daltons. Preferably, the proanthocyanidins used in the compositions of the present invention are procyanidins and have a molecular weight range of about 900 to about 1800 Daltons or a molecular weight range of about 1150 to about 1750 Daltons.

Where molecular weight ranges are described in this application they are intended to refer to the weight of the $[M-H]^-$ ion based on the m/z ratio. For the determination of molecular weight, negative ion mass spectrometry is preferred. Mass spectrometry may be performed as part of HPLC i.e. as HPLC-MS/MS. Such methods are well known in the art, see for example, *Annals of the New York Academy of Science*, 2002, 957: 78-89; *Journal of Agricultural Food Chemistry*, 2002, 50: 5191-96; *Nature*, 2006, 444:566; *Molecules*, 2012, 17:14821-40.

In one embodiment, the proanthocyanidins used in the compositions of the present invention are derived from apple, cocoa bean, cranberry, grape seed, hawthorn, maritime pine bark, or sorghum.

Preferably, the proanthocyanidins used in the compositions of the present invention are derived from apple or grape seed. More preferably, the proanthocyanidins used in the compositions of the present invention are procyanidins and are derived from apple or grape seed.

In one embodiment, the proanthocyanidins used in the compositions of the present invention are derived from grape seeds and are galloylated. Preferably, the proanthocyanidins used in the compositions of the present invention are procyanidins derived from grape seeds and are galloylated.

Ellagitannins are also referred to as hydrolysable tannins. Ellagitannins are polymeric derivatives of gallic acid that are esters of a sugar (*Natural Products Report* 2009, 26:1001-1043). Example ellagitannin compounds are oenothein B, agrimoniin, camelliatannin H, camellioferin A, castalagin, castalin, casuarictin, degalloylrugosin F, grandinin, heterophylliin B, heterophylliin C, punicalagin, punicalin, roburin A, rugosin A, rugosin D, rugosin E, sanguiin H3, sanguiin H6, sanguiin H10, tellimagrandin II, terflavin B and vescalagin.

Pomegranate fruits, the fruits of *Punica granatum*, are a rich source of ellagitannins. The identified ellagitannins in pomegranate juice and seeds include monomers such as punicalagin, punicalin, and punicacortein C, and oligomers such as oenothein B (dimer), eucalbanin B (dimer), and eucarpanin $T_1$ (trimer), pomegraniin A (tetramer) and pomegraniin B (pentamer).

In one embodiment, the ellagitannins used in the compositions of the present invention are derived from pomegranate fruits.

Preferably, the ellagitannins used in the compositions of the present invention are derived from pomegranate fruits and contain at least one molecule selected from the group consisting of punicalin, punicacortein C, oenothein B, eucalbanin B and eucarpanin $T_1$, or isomers of these ellagitannins.

Oenothein B is a particularly preferred ellagitannin for use in the compositions of the invention. As indicated above, pomegranate fruits are one source of oenothein B. Thus, in one embodiment, the ellagitannins used in the compositions of the present invention are derived from pomegranate fruits and contain oenothein B.

Other sources of oenothein B include leaves of plants in the *Epilobium* genus. As used herein, the term "*Epilobium* genus" should be understood to include all plants in the *Epilobium* genus. This definition also includes genetically modified species having increased oenothein B content. Such genetically modified species may be engineered by a specific breeding program (i.e. to improve polyphenol content) or may be naturally occurring hybrids. It is known that plants in the *Epilobium* genus have a tendency to hybridise, and in the UK it has been reported that hybrid varieties are more common than non-hybridised varieties. Examples of the *Epilobium* genus include *Epilobium angustifolium* (rosebay willowherb), *Epilobium montanum* (broad-leaved willowherb), and *Epilobium parviflorum* (smallflower hairy willowherb). The ellagitannins derived from the leaves of *Epilobium parviflorum* (smallflower hairy willowherb) are particularly preferred. Thus, in one embodiment, the ellagitannins used in the compositions of the present invention are those derived from plants of the *Epilobium* genus and contain oenothein B.

In one embodiment, the ellagitannins used in the compositions of the present invention are derived from the leaves of *Epilobium* species *Epilobium angustifolium* (rosebay willowherb), *Epilobium montanum* (broad-leaved willowherb), and *Epilobium parviflorum* (smallflower hairy willowherb) and include the ellagitannin oenothein B. The ellagitannins derived from the leaves of *Epilobium parviflorum* (smallflower hairy willowherb) are particularly preferred.

Oenothein B can also be obtained from other sources, including *Oenothera erythrosepala* (evening primrose) and a variety of myrtaceous plants including plants in the Myrtaceae, Lythraceae, Onagraceae, Melastomataceae and Combretaceae familes (*International Journal of Molecular Sciences* 2010, 11: 79-106).

As indicated above, one approach to the treatment of endothelial dysfunction is by induction of KLF2 to improve vascular function. It is known that some procyanidins increase KLF2 mRNA levels, and it has been suggested that inducers of KLF2 would have utility as agents to prevent atherosclerosis (*Cardiovascular Pathology,* 2013; 22:9-15). However, use of an ellagitannin to increase KLF2 has not been demonstrated in the literature. The applicant has surprisingly found that combining procyanidins with ellagitannins results in an unusually sustained induction of KLF2. This effect is particularly marked when the ellagitannin is oenothein B (see FIG. 2 discussed infra).

Oenothein B has the following structure:

The molecular weight of the (M-H) ion of oenothein B is 1567.

In one embodiment, the ellagitannins used in the compositions of the present invention are derived from the fruits of *Rubus* species and include the ellagitannin sanguiin H6.

Fruits of *Rubus* species include raspberries, blackberries, loganberries, boysenberries, tayberries and cloudberries. Raspberries are particularly preferred.

In one embodiment, the ellagitannins used in the compositions of the present invention are derived from the leaves of *Epilobium* species and include the ellagitannin oenothein B.

In one embodiment, the ellagitannins used in the compositions of the present invention are derived from the fruits of *Rubus* species and include the ellagitannin sanguiin H6.

In one embodiment, the ellagitannins used in the compositions of the present invention have a molecular weight range of about 1000 to about 3000 Daltons.

In another embodiment, the ellagitannins used in the compositions of the present invention have a molecular weight range of about 1250 to about 2500 Daltons or a molecular weight range of about 1500 to about 1900 Daltons.

In a preferred embodiment, the ellagitannins used in the compositions of the present invention are derived from pomegranate fruits and have a molecular weight range of about 1000 to about 3000 Daltons.

More preferably, the ellagitannins used in the compositions of the present invention are derived from pomegranate fruits and have a molecular weight range of about 1500 to about 1900 Daltons.

In a preferred embodiment, the ellagitannins used in the compositions of the present invention are derived from the fruits of *Rubus* species and have a molecular weight range of about 1000 to about 3000 Daltons.

More preferably, the ellagitannins used in the compositions of the present invention are derived from the fruits of *Rubus* species and have a molecular weight range of about 1500 to about 1900 Daltons. Most preferably, said fruits of *Rubus* species are raspberry fruits.

In a preferred embodiment, the ellagitannins used in the compositions of the present invention are derived from the leaves of any plant forming part of the *Epilobium* genus and have a molecular weight range of about 1500 to about 2000 Daltons. Preferably, said *Epilobium* plant is *Epilobium parviflorum* (smallflower hairy willowherb).

Even more preferably, in the compositions of the invention, the at least one ellagitannin is oenothein B and the at least one proanthocyanidin is a mixture comprising procyanidin trimers, procyanidin tetramers, procyanidin pentamers and/or procyanidin hexamers.

In one embodiment, in the compositions of the invention, the weight ratio of the at least one ellagitannin to the at least one proanthocyanidin is in the range of about 1:10 to about 10:1, such as about 1:9 to about 9:1. Preferably, the at least one proanthocyanidin is at least one procyanidin.

Preferably, in the compositions of the invention, the weight ratio of the at least one ellagitannin to the at least one proanthocyanidin is in the range of about 1:5 to about 5:1, including from about 1:4 to about 4:1 and from about 1:3 to about 3:1 and from about 1:2 to about 2:1. Preferably, the at least one proanthocyanidin is at least one procyanidin.

As previously indicated, natural sources of polyphenols include common foodstuffs such as tea, coffee, cocoa, red wine, beer, cider, fruits, vegetables and nuts, as well as various plants that may be used as herbal medicines. The polyphenols used in the compositions, uses and methods of the present invention can be extracted from e.g. whole fruit, nuts and leaves. However, it is also possible to use "waste products" in order to extract the desired polyphenol compounds. Typical "waste products" include any solid residue remaining after e.g. juicing whole fruit, such as skin, seeds and pulp. Isolating polyphenol compounds from waste products has considerable commercial advantages.

Preferably, the compositions of the present invention also comprise citrulline or a citrulline salt and/or aspartic acid or an aspartate.

Citrulline, as a by-product of nitric oxide synthesis, is rapidly recycled intracellularly to L-arginine by argininosuccinate synthase. Citrulline recycling by argininosuccinate synthase also requires aspartic acid or aspartate as a co-substrate. Without wishing to be bound by theory, it is believed that compositions comprising citrulline or a citrulline salt and/or aspartic acid/aspartate will boost the levels of L-arginine available for NO production, as synthesis of argininosuccinate synthase is believed to be upregulated by proanthocyanidins, and in particular, by procyanidins.

In a particularly preferred embodiment, the compositions of the invention comprise at least one ellagitannin in combination with at least one proanthocyanidin, citrulline or a citrulline salt and aspartic acid or an aspartate, wherein the proanthocyanidin has a molecular weight of about 800 to about 1900 Daltons and wherein the ellagitannin has a molecular weight of about 1000 to about 3000 Daltons, more preferably a molecular weight of 1500 to 1900 Daltons.

In more preferred embodiment, the compositions of the invention comprise at least one ellagitannin in combination with at least one proanthocyanidin, citrulline or a citrulline salt and aspartic acid or an aspartate, wherein the at least one proanthocyanidin is at least one procyanidin and has a molecular weight of about 800 to about 1900 Daltons and wherein the ellagitannin has a molecular weight of about 1000 to about 3000 Daltons, more preferably a molecular weight of 1500 to 1900 Daltons.

In a most preferred embodiment, the compositions of the invention comprise oenothein B as the at least one ellagitannin in combination with at least one procyanidin wherein the at least one procyanidin is a mixture of procyanidin trimers, procyanidin tetramers, procyanidin pentamers and/or procyanidin hexamers, and the composition further comprises citrulline or a citrulline salt and aspartic acid or an aspartate.

In another embodiment, the compositions of the invention consist essentially of at least one ellagitannin in combination with at least one proanthocyanidin, citrulline or a citrulline salt and aspartic acid or an aspartate, wherein the proanthocyanidin has a molecular weight of about 800 to about 1900 Daltons and wherein the ellagitannin has a molecular weight of about 1000 to about 3000 Daltons, more preferably a molecular weight of 1500 to 1900 Daltons.

In another embodiment, the compositions of the invention consist essentially of at least one ellagitannin in combination with at least one proanthocyanidin, citrulline or a citrulline salt and aspartic acid or an aspartate, wherein the at least one proanthocyanidin is at least one procyanidin and has a molecular weight of about 800 to about 1900 Daltons and wherein the ellagitannin has a molecular weight of about 1000 to about 3000 Daltons, more preferably a molecular weight of 1500 to 1900 Daltons.

In a further embodiment, the compositions of the invention consist essentially of oenothein B as the at least one ellagitannin, at least one proanthocyanidin that is a mixture of procyanidin trimers, procyanidin tetramers, procyanidin pentamers and/or procyanidin hexamers, citrulline or a citrulline salt and aspartic acid or an aspartate.

In one embodiment, the compositions of the present invention may be used in preventing or treating diseases associated with endothelial dysfunction including arteriosclerosis, hypertension, pulmonary hypertension, coronary artery disease, chronic heart failure, peripheral artery disease, diabetes, chronic renal failure and erectile dysfunction.

Preferably, the compositions of the present invention may be used in treating arteriosclerosis of the coronary arteries, carotid arteries or peripheral arteries.

Preferably, the compositions of the present invention may be used in treating hypertension.

Preferably, the compositions of the present invention may be used in treating pulmonary hypertension.

Preferably, the compositions of the present invention may be used in treating coronary artery disease.

Preferably, the compositions of the present invention may be used in treating chronic heart failure.

Preferably, the compositions of the present invention may be used in treating peripheral artery disease.

Preferably, the compositions of the present invention may be used in treating diabetes.

Preferably, the compositions of the present invention may be used in treating chronic renal failure.

Preferably, the compositions of the present invention may be used in treating erectile dysfunction.

In one embodiment, the compositions of the present invention may be used to enable ergogenic effects, preferably leading to more sustained athletic performance. Thus, in one embodiment the compositions of the invention may be used as ergogenic aids.

In one embodiment, the compositions of the present invention may be used as prophylactics in order to prevent or delay the onset of endothelial dysfunction in patients at risk thereof.

In a further embodiment, the present invention is directed to use of a composition of the invention for the prevention or treatment of endothelial dysfunction.

In a further embodiment, the present invention is directed to use of a composition of the invention in the manufacture of a medicament for use in the prevention or treatment of endothelial dysfunction.

In a further embodiment, the present invention is directed to a method of treating endothelial dysfunction comprising administering to a patient in need thereof, either simultaneously or sequentially, at least one ellagitannin in combination with at least one proanthocyanidin, preferably wherein the at least on proanthocyanidin is at least one procyanidin. In the case of simultaneous administration, this may be in the form of a pharmaceutical composition of the invention.

The present invention is further directed to a process of preparing the proanthocyanidin and ellagitannin compositions of the invention.

Thus, in one embodiment, the present invention is directed towards a process for preparing a composition comprising at least one ellagitannin in combination with at least one proanthocyanidin, wherein said process comprises mixing at least one proanthocyanidin and at least one ellagitannin. Preferably, the at least one proanthocyanidin is at least one procyanidin.

In an embodiment, the present invention is directed to a process as described above wherein the process further comprises the addition of citrulline or a citrulline salt and aspartic acid or aspartate. This addition may occur simultaneously with, or separately from, the mixing of the said ellagitannin and said proanthocyanidin, and in any order.

In an embodiment, the process of the present invention further involves the addition of at least one pharmaceutically acceptable excipient or carrier. Addition of the pharmaceutically acceptable excipient or carrier may occur simultaneously with, or separately from, the mixing of the said ellagitannin and said proanthocyanidin, and in any order.

In an embodiment a first composition comprising at least one proanthocyanidin is prepared by the following steps:
(a) elution of crude proanthocyanidin-containing polyphenol extract through an adsorbent matrix; and then
(b) rinsing said matrix to remove unbound material; and then
(c) eluting an enriched polyphenol extract using a suitable solvent.

In an embodiment a second composition comprising at least one ellagitannin is prepared by the following steps:
(d) elution of crude ellagitannin-containing polyphenol extract through an adsorbent matrix under conditions that permit polyphenol binding to the matrix; and then
(e) rinsing said matrix to remove unbound material; and then
(f) eluting an enriched polyphenol extract using a suitable solvent.

According to an embodiment of the process of the invention, said first composition and said second composition may then be mixed to prepare a composition of the invention.

The absorbent matrix for use in steps (a) and (d) may take any suitable form. However, it is preferred that the absorbent matrix is a bead formed medium, for example a dextran or acrylic bead formed medium. Sephadex® LH20 (available from Sigma Aldrich) is an example of a preferred dextran bead formed medium. The beads of absorbent matrix are typically packed into a column or filter pad, onto which the crude polyphenol containing extract is loaded and elution is performed. Elution may take place under gravity. However, for reasons of process efficiency, it is preferable to use a low amount of pressure to force the eluent through the column/pad of absorbent matrix. Steps (a) and (d) are mostly likely performed at room temperature. However, the skilled person would readily be able to select suitable elution conditions (i.e. solvent, temperature and pressure) based on e.g. the scale of the process, the desired polyphenol product and the chemical stability thereof.

In a preferred embodiment, the absorbent matrix for use in steps (a) and (d) is Sephadex® LH20.

In a preferred embodiment, the elution solvent for steps (a) and (d) is an acidic aqueous organic solvent.

Preferably, said aqueous organic solvent is aqueous acetone. Preferably, acidification is carried out using acetic acid. Thus, in a preferred embodiment, the elution solvent for use in steps (a) and (d) is an aqueous acetic acid/acetone solution.

In a preferred embodiment, the rinsing solvent for use in steps (b) and (e) is an organic aqueous acid. Preferably, said organic aqueous acid is acetic acid.

In a further embodiment, the processes for preparing the first and second compositions may comprise an additional rinsing step steps after steps (b) and (e) using an aqueous acetic acid/acetone solution.

In a preferred embodiment, the eluting solvent for use in steps (c) and (f) is aqueous acetone, which may have a reduced pH due to the addition of an appropriate acid. Thus, the eluting solvent for use in steps (c) and (f) may be an aqueous acetic acid/acetone solution.

In a further embodiment, the elution conditions for steps (c) and (f) can be selected to enable further enrichment of the desired polyphenols, e.g. those with the greatest biological activity.

In a further embodiment, additional purification of the polyphenol compositions obtained by the above-described processes can be carried out by general methods known in the art, such as HPLC (either normal phase or reverse phase).

Dosage and Formulation

The present application provides compositions comprising certain polyphenol compounds that may be used for the prevention or treatment of endothelial dysfunction. The dosage regimen for the compositions of the present invention will, of course, vary depending upon factors such as the route of administration, the age, sex, health, medical condition and weight of the recipient; the nature and extent of the symptoms; the nature of any concurrent treatment; the frequency of treatment; the route of administration and the effect desired. In particular it is noted that compositions of the present invention may be formulated for use in therapy, or for use as a prophylactic or as an ergogenic aid.

Compositions of this invention may be administered in a single daily dose, or the total daily dosage may be administered in divided doses two, three, or four times daily.

In an embodiment of the invention, desired polyphenol compounds are microencapsulated, either separately or together, to increase stability, or bioavailability or to mask taste. Preferably, microencapsulation is carried out using water-in-oil microencapsulation technology for liquid formulations (see U.S. Pat. No. 8,685,446 B2) or using a three component microencapsulation mixture of maltodextrin, mesquite gum, and zein, which is spray dried for solid or powder formulations (see *Food and Bioprocess Technology*, 2013, 6: 941-51).

In an embodiment of the invention, the compositions can be in the form of any pharmaceutically acceptable formulations such as tablets, capsules, buccal tablets, orally disintegrating tablets, oral fast dissolving tablets, dispersible tablet, masticatory, granules, dry suspension, injection, solution, slow-release formulation, controlled-release formulation, rapid-release formulation, etc.

In an embodiment, pharmaceutical compositions of the invention also include one or more pharmaceutically acceptable excipients or carriers.

In an embodiment of the invention, the compositions can be prepared as part of a nutraceutical product, for example as a snack bar or a pre-prepared drink/powdered drink formula.

In an embodiment of the invention, the compositions of the invention may advantageously comprise further components such as vitamins, minerals and/or fibre. Suitable vitamins and minerals include, but are not limited to, the B vitamins, vitamin C, folic acid, calcium, iron, magnesium, zinc, selenium, niacin, vitamin D, vitamin A, vitamin E, chromium, copper, manganese, boron, molybdenum, omega fatty acids and co-enzyme Q10. Mixtures of such additional components may be advantageous. For example, in patients with cognitive impairment, it may be advantageous to combine compositions of the invention with a source of omega 3 fatty acids and vitamin B12. Where the compositions are intended for use as ergogenic aids, formulation with a protein source, such as whey powder, may be desirable.

By way of example, the daily dosage of proanthocyanidins (preferably procyanidins) in the compositions of the invention is from about 100 mg to about 1000 mg, preferably about 250 to about 500 mg. The daily dosage of ellagitannins in the compositions of the invention is from about 50 mg up to about 1000 mg, preferably about 100 to about 500 mg.

Where citrulline or a citrulline salt is present in compositions of the present invention, the daily dosage is preferably about 850 mg to about 18000 mg, more preferably about 3750 to about 8750 mg per day.

Where L-aspartic acid or aspartate is present in compositions of the present invention, the daily dosage is preferably about 650 mg to about 14000 mg, more preferably about 2600 to about 6700 mg.

Preferably, the compositions of the invention may comprise L-citrulline and L-aspartate in a total amount of about 1500 mg to about 32000 mg, preferably about 5800 to about 14500 mg, where the amounts in mg represent the total daily dosage.

EXAMPLES

The following non-limiting Examples further illustrate the present invention.

For ease of reference, the following abbreviations are used herein:
$A_{263}$—absorbance at 263 nm
ANOVA—analysis of variance statistical test
Ap-OPC—apple oligomeric procyanidins
Biotin-Ap-OPC—biotinylated apple oligomeric procyanidins
cm—centimeter
dP—degree of polymerisation (1=monomers to 10=decamers)
EllagiTs—ellagitannins
em—emission
eNOS—endothelial nitric oxide synthase
ET-1—endothelin-1
ex—excitation
g—gram
GS-OPC—grape seed oligomeric procyanidins
h—hour
HPLC—high performance liquid chromatography
kg—kilogram
KLF2—Kruppel-like factor 2
l—liter
LC-MS/MS—liquid chromatography-tandem mass spectrometry
mg—milligram
µg—microgram
min—minute
ml—milliliter
mM—millimolar
µm—micrometer
µmol—micromolar
mRNA—messenger ribonucleic acid
mV—millivolts
NO—nitric oxide
nm—nanomolar
n.s.—non significant
OPC—oligomeric procyanidins
OTb—oenothein B
P—p-value, statistical significance
PTFE—polytetrafluoroethylene
qRT-PCR—quantitative reverse transcription polymerase chain reaction
Rb-ET—raspberry ellagitannins
SD—standard deviation
TMB—3,3',5,5'-tetramethylbenzidine, chromogenic substrate
UHPLC—ultra high performance liquid chromatography
UV—ultraviolet Example 1: Extraction and Partial Purification of Raspberry Ellagitannins Aqueous acetone (70% in water), 3 l, is added to fresh seeds of red raspberries (approx. 2 kg) in a 5 l polypropylene beaker and mixed for 1 h at room temperature with a magnetic stirrer. The crude seed extract is filtered through a porous PTFE filter to separate the raspberry polyphenol extract (approx. 2.5 l) from particulate material. The resultant solution of raspberry polyphenols is diluted with 10 mM acetic acid (7.5 l) and pumped onto a column of Sephadex® LH20 (5×15 cm), which has been pre-equilibrated with 10% acetone in 10 mM acetic acid. The column is rinsed by pumping through 1 l of 10 mM acetic acid, followed by 1 l of 20% acetone in 10 mM acetic acid. Elution of raspberry ellagitannins is achieved by pumping 2 l 50% acetone in water. Fractions (200 ml) are collected. Fractions are monitored for polyphenol content by UV absorption measurements at 280 nm, and colorimetric assay measurements of polyphenols using Folin-Ciocalteu reagent (phosphomolybdate/phosphotungstate mixture). Fractions are also monitored for biological activity in relation to modifying endothelial function by assessing the relative potency of each fraction for inhibiting endothelin-1 synthesis by cultured endothelial cells.

The principles of this method can be adapted for pomegranate pericarp extraction. Aqueous acetone (70% in water), 600 ml, is added to finely chopped pomegranate pericarp (200 g). After filtration the filtrate (approx. 500 ml) is diluted with 10 mM acetic acid (1.5 l) and pumped onto a column of Sephadex® LH20 (5×15 cm). Subsequent steps are as described above.

Example 2: HPLC Purification of Fractions from Adsorption Chromatography

Peak fractions eluted with 50% aqueous acetone from Sephadex® LH20 are concentrated under vacuum to remove acetone. The concentrated extract is pumped onto a column of C18 silica (5×25 cm) at a flow rate of 50 ml/min. The column is rinsed with 1 liter of 8% methanol, and then eluted with 1.5 liter linear gradient to 25% methanol to obtain an enriched ellagitannin extract. 100 ml fractions are collected during elution. Fractions are monitored for polyphenol content by UV absorption measurements at 280 nm, and colorimetric assay measurements of polyphenols using Folin-Ciocalteu reagent (phosphomolybdate/phosphotungstate mixture). Fractions are also monitored for biological activity in relation to modifying endothelial function by assessing the relative potency of each fraction for inhibiting endothelin-1 synthesis by cultured endothelial cells. Peak fractions, based on ability to inhibit endothelin-1 synthesis, are pooled and dried.

Example 3: Purification of Apple Procyanidins 20 g of crude apple polyphenol extract powder (75% polyphenol extract from A. M. Todd Botanical Therapeutics, Kalamazoo, Mich., USA) is dissolved in 500 ml 10% acetone in 10 mM acetic acid. The crude extract is pumped onto a column of Sephadex LH20 (5×15 cm). Subsequent steps are as described above. The column is then rinsed and eluted with 50% aqueous acetone as described in Example 1. The yield of procyanidins is 7 g (35%). Relative potency of the purified extract compared to the starting material is determined by comparing inhibitory effects on endothelin-1 synthesis by endothelial cells. The proportion of procyanidin tetramers to hexamers in the purified extract, compared to the starting material, is assessed by HPLC using a Develosil® 100 Diol column (5 µm, 4.6×250 mm, available from www.develosil.com). Such methods are well known in the art, see e.g. *Journal of Agricultural and Food Chemistry* 2009, 57: 1896-902 and *Journal of Chromatography A,* 2009, 1216, 4831-4840. The purified apple procyanidins are pooled and dried.

Example 4: HPLC and LC-MS/MS Analysis of Polyphenols

The procyanidin content of extracts is analysed by HPLC using a Develosil 100 Diol column (5 µm, 4.6×250 mm) with procyanidins monitored by fluorescence (ex 276 nm, em 316 nm) using gradient elution with acetonitrile/acetic acid/methanol/water. The identities of the eluted procyanidins can be further confirmed by connecting this HPLC system to a mass spectrometer for MS/MS analyses.

Ellagitannin compositions of extracts are analysed by reverse phase HPLC using a UHPLC column of C18 silica (2×50 mm) connected to a mass spectrometer for MS/MS analyses (as per the methods described in *Molecules,* 2012, 17:14821-40).

Example 5: Inhibition of Endothelin-1 Synthesis by Endothelial Cells

The effects on endothelin-1 synthesis of purified procyanidins and ellagitannins, either alone or in combination, are tested on human, bovine or porcine aortic endothelial cells cultured in multi-well plates. Cells are grown in a $CO_2$ incubator with specific growth media until becoming confluent. Purified extracts, chromatography fractions, or isolated procyanidins and ellagitannins are evaluated after dilution in cell culture media and then incubated for up to 24 h with the cultured cells. At the end of the incubation period cell culture media samples are collected, and endothelin-1 synthesis is determined by immunoassay of the media samples. ET-1 release for each treated well is expressed as a percentage of basal release from control wells containing cells incubated with cell culture medium alone. Data are compared and analysed for statistically significant differences using life sciences software such as Graphpad Prism (available from www.graphpad.com). At the end of the incubation period cells are lysed to obtain mRNA to measure changes in gene expression that indicate improved endothelial function. Analyses of relative levels of mRNA transcripts are undertaken by quantitative reverse transcription polymerase chain reaction (qRT-PCR) (*Journal of Agricultural and Food Chemistry,* 2010, 58: 4008-13).

Example 6: Stimulation of Nitric Oxide Synthesis by Endothelial Cells

Confluent cultures of endothelial cells are prepared as described in example 5. Acute changes in nitric oxide synthesis can be stimulated with the calcium ionophore A23187 (0.1-1 µM), after cells have been preincubated for up to 24 h with purified procyanidins and ellagitannins, either alone or in combination. The influence of citrulline and aspartate on NO synthesis is evaluated by adding citrulline (0.05-1 mM) alone or in combination with aspartic acid (0.05-1 mM) to the cell culture medium during periods when NO measurements are made. NO measurements are made by assaying total nitrite and nitrate in conditioned media samples using the Griess reaction, monitored spectrophotometrically at 540 nm; or by measurement of NO by fluorescence with DAF-2 (4,5-diaminofluorescein) (FEBS Letters 1998, 427: 263-266). At the end of incubations cells can be lysed for measurement of eNOS protein by western blot as index of eNOS activity.

Example 7: Endothelium-Dependent Vasodilatation of Blood Vessels

Isolated blood vessels sections are prepared from rat aorta and cut into rings, carefully avoiding damage to the endothelium. Vascular rings are individually suspended in organ baths and bathed in Krebs-Ringer solution. Vascular rings are attached to isometric transducers to measure vascular tone. After a period of equilibration the rings of aorta are pre-contracted with phenylephrine (1 µmol/l) and the presence of a functional endothelium is verified with acetylcholine (10 µmol/l). Relative effectiveness of procyanidins and ellagitannins as inducers of endothelium-dependent vasodilatation is assessed by constructing cumulative concentration response curves with purified procyanidins and ellagitannins, either alone or in combination. Citrulline (0.05-1 mM) is added alone or in combination with aspartic acid (0.05-1 mM) to the organ bath solution prior to addition of procyanidin/ellagitannin combinations and compared to the same concentrations of procyanidin and ellagitannin without citrulline and aspartic acid. Data are compared and analysed for statistically significant differences using life sciences software such as Graphpad Prism.

Example 8: Pharmaceutical Product for Treatment of Chronic Heart Failure

A tablet or capsule pharmaceutical formulation is made containing 125 mg purified raspberry ellagitannins as per Example 2 and 125 mg purified apple procyanidins as per Example 3, plus appropriate pharmaceutical excipients. Two to eight tablets are to be taken per day. Biomarker monitoring of the response to treatment may be made by measurements of N-terminal pro-B-type natriuretic peptide at monthly intervals.

Example 9: Pharmaceutical Product for Treatment of Chronic Heart Failure

A tablet or capsule pharmaceutical formulation is made containing 125 mg purified *Epilobium* ellagitannins including oenothein B and 125 mg purified apple procyanidins as per Example 3, plus appropriate pharmaceutical excipients. Two to eight tablets are to be taken per day. Biomarker monitoring of the response to treatment may be made by measurements of N-terminal pro-B-type natriuretic peptide at monthly intervals.

Example 10: Microencapsulation of Procyanidins and Ellagitannins

To increase stability, mask flavour and increase bioavailabilty, ellagitannins and procyanidins are microencasulated using water-in-oil microencapsulation technology for liquid products; or maltodextrin, mesquite gum with zein and spray dried for a powder product. These microencapsulated polyphenols can be incorporated directly into liquid products such as in Examples 11 and 12, or the spray dried microencapsulated polyphenols can be incorporated into dry powder products such as in Examples 13 and 14.

Example 11: Drink Product for Treatment of Hypertension 250 mg raspberry ellagitannins obtained by the method of Example 2 and 250 mg apple procyanidins obtained by the method of Example 3 are microencapsulated. To this mixture is added 4 g citrulline and 3 g aspartic acid. The mixture is diluted with 50 ml of water containing pH stabilisers, sweeteners and flavourings. One to two drinks of 50 ml may be consumed per day.

Example 12: Drink Product for Treatment of Hypertension 250 mg ellagitannins obtained from pomegranate (including oenothein B) and 250 mg procyanidins obtained from grape seed extract are microencapsulated. To this mixture is added 4 g citrulline and 3 g aspartic acid. For use, the mixture is diluted with 50 ml of water containing pH stabilisers, sweeteners and flavourings. One to two drinks of 50 ml may be consumed per day.

Example 13: Ergogenic Product for Improving Athletic Performance and Duration of Maximum Performance Dried powder in a sachet containing lyophilised microencapsulated 500 mg raspberry ellagitannins and 500 mg apple procyanidins obtained via the methods described in Examples 2 and 3 are mixed in powder form with citrulline 5 g, aspartic acid 4 g, soya protein hydrolysate powder 25 g, L-carnitine tartrate 2 g, ascorbic acid 30 mg, tocopherol acetate 5 mg, and appropriate flavourings and/or sweetener as required.

For use, the full contents of a sachet are mixed with 300 ml water. One to two sachets may be consumed per day.

Example 14: Ergogenic Product for Improving Athletic Performance and Duration of Maximum Performance Dried powder in a sachet containing lyophilised microencapsulated 500 mg ellagitannins obtained from pomegranate (including oenothein B) and 500 mg procyanidins obtained from grape seed extract are mixed in powder form with citrulline 5 g, aspartic acid 4 g, soya protein hydrolysate powder 25 g, L-carnitine tartrate 2 g, ascorbic acid 30 mg, tocopherol acetate 5 mg, and appropriate flavourings and/or sweetener as required.

For use, the full contents of a sachet are mixed with 300 ml water. One to two sachets may be consumed per day.

Example 15: Inhibition of Endothelin-1 Synthesis by Oenothein B

Figure 1:
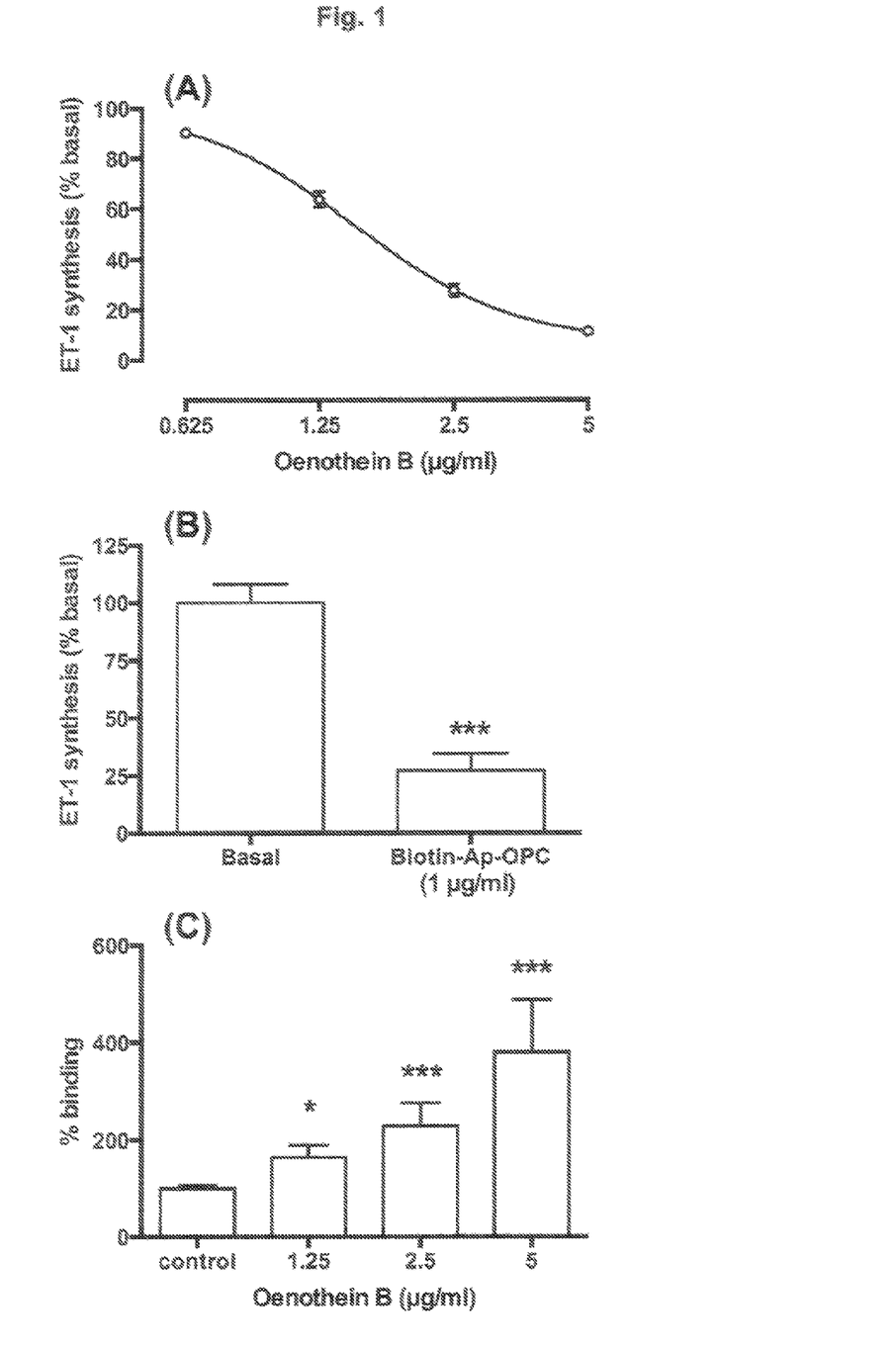
FIG. 1: Biological activity of oenothein B and effect of oenothein B on binding of procyanidins to endothelial cells.

Oenothein B (>95% purity) was purified from pomegranate juice by Sephadex LH20 chromatography and reverse-phase HPLC (step 1—Apex Prepsil 8 µm C-18 10×250 mm HPLC column—Jones Chromatography; step 2 Luna 5 µm PFP(2) 4.6×250 mm HPLC column—Phenomenex). Ability to modify endothelial function was assessed by incubating oenothein B with bovine aortic endothelial cells and measuring endothelin-1 synthesis following previously described methods (*Journal of Agricultural and Food Chemistry*, 2010, 58: 4008-13). As shown by FIG. 1(A), inhibition of endothelin-1 synthesis by oenothein B was found to be concentration dependent.

Example 16: Inhibition of Endothelin-1 Synthesis by Biotinylated Apple Oligomeric Procyanidins (Biotin-OPC)

Biologically active biotin-labelled apple oligomeric procyanidins were prepared as follows: apple polyphenol extract was fractionated on Sephadex LH20 to obtain a fraction enriched in apple oligomeric procyanidins (OPC) tetramers to hexamers. The fraction was dried, re-dissolved in dimethyl formamide and reacted with the tetrafluorophenyl ester of triethyleneglycol-biotin (Thermo Scientific EZ-Link™ TFP-PEG3-Biotin). The resultant biotinylated-OPC product was purified by HPLC and retention of biological activity was confirmed using bovine aortic endothelial cells by measuring inhibition of endothelin-1 synthesis. As shown by FIG. 1(B), inhibition of endothelin-1 synthesis by biotinylated apple oligomeric procyanidins was observed.

Example 17: Increased Binding of Biotinylated OPC to Endothelial Cells

Bovine aortic endothelial cells were incubated with oenothein B (µg/ml) from pomegranate juice for 30 min before addition of biotinylated-OPC (1 µg/ml) alone or with oenothein B (µg/ml) for 30 min. After removal of the incubation mixture, bound biotinylated-OPC was detected by incubation with neutravidin-horseradish peroxidase for 1 h; followed by addition of TMB substrate for 30 min after cells had been rinsed twice to remove excess neutravidin-horseradish peroxidase. Binding is indicated relative to biotinylated-OPC alone after subtraction of background signal. (All data are shown as mean±SD; *=P<0.05; =P<0.01; *=P<0.001 indicates significant differences from basal or control values). As shown by FIG. 1(C), binding of procyanidins increases as oenothein B concentration increases. From this it can be concluded that oenothein B increases the affinity of endothelial cells for procyanidins, and enhances the effectiveness of procyanidins for reversing endothelial dysfunction.

Example 18: Effect of Oenothein B, Ellagitannin Extracts, Procyanidins and Mixtures Thereof on Endothelial Cell Synthesis of Endothelin-1

Figure 3:
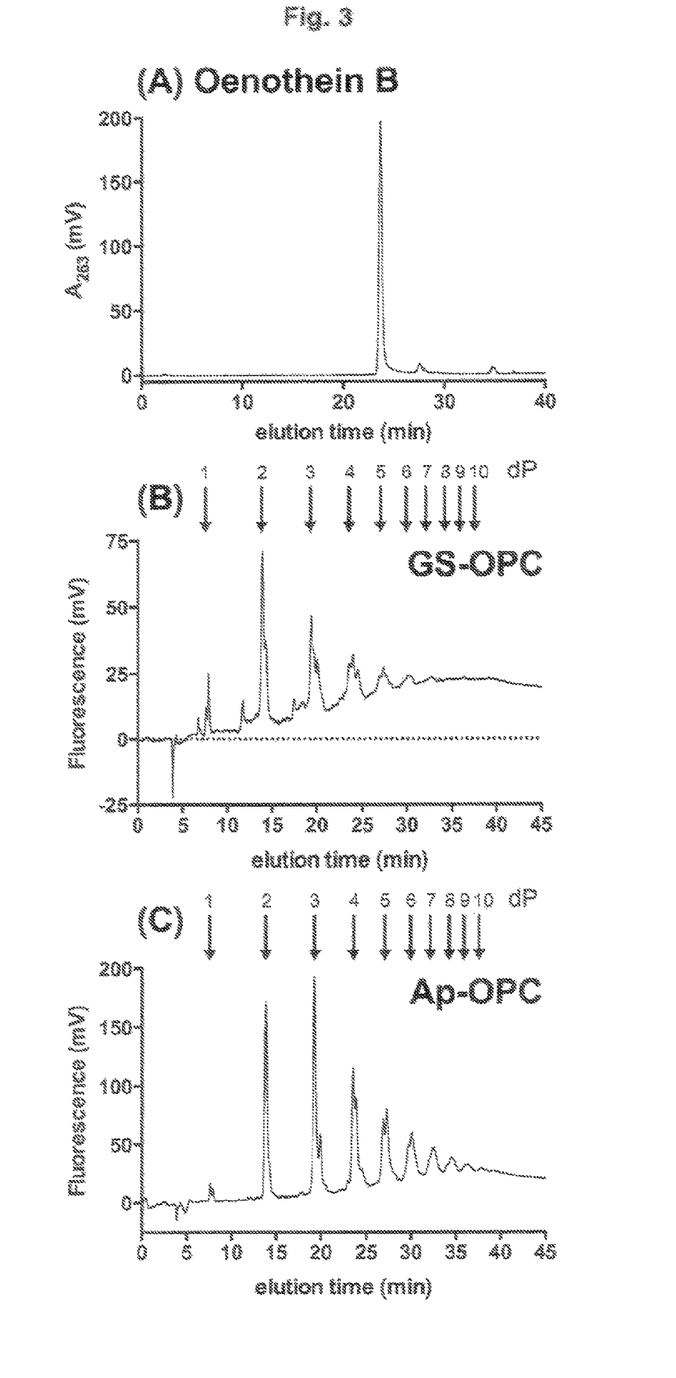
FIG. 3: HPLC characterisation of oenothein B, and of procyanidin-enriched grape seed and apple extracts.

Oenothein B (OTb, >90% purity) was purified from extracts of *Epilobium* by Sephadex LH20 chromatography and reverse phase C-18 HPLC (Apex Prepsil 8 µm C-18 10×250 mm HPLC column—Jones Chromatography). Analysis of purity was performed by HPLC using a Luna 5 µm PFP(2) 4.6×250 mm HPLC column (Phenomenex) by gradient elution at 1 ml/min with methanol (0-10% over 2 min, 10-25% over 30 min, and 25-80% over 10 min) in 10 mM acetic acid, UV absorbance was measured at 263 nm, FIG. 3(A). Raspberry ellagitannin extract (Rsb) was prepared from raspberry seeds (see EXAMPLE 1). Grape seed extract procyanidins were prepared from MegaNatural Gold grape seed extract (Polyphenolics Inc, Madera, Calif., USA), by fractionation on Sephadex LH20, with the enriched fraction of grape seed procyanidins (GS-OPC) being eluted with 50% acetone. The composition of GS-OPC was determined by HPLC using a 100Diol-5 Develosil™ HPLC column (Nomura Chemical Co. Ltd, Japan) with gradient elution at 0.8 ml/min: the column was equilibrated with 95% buffer A/5% buffer B and eluted with a gradient to 40% buffer B over 35 min and maintained at 40% buffer B for 10 min (buffer A—98% acetonitrile/2% acetic acid; buffer B—95% methanol/3% water/2% acetic acid) and monitored by fluorescence Ex 276 nm/Em 336 nm). The composition of GS-OPC was enriched in oligomeric procyanidins in the trimer to hexamer range (OPC trimer to hexamer >50%; detailed composition: monomer 3%, dimer 18%, trimer 16%, tetramer 16%, pentamer 12%, hexamer 8% heptamer 6%, unresolved OPC≈20%) FIG. 3(B). Apple OPC were fractionated on Sephadex LH20 to enrich the composition of oligomeric procyanidins in the trimer to hexamer range (OPC trimer to hexamer 70.6%; detailed composition: monomer 1.6%, dimer 18.0%, trimer 24.9%, tetramer 20.4%, pentamer 15.2%, hexamer 10.1% heptamer 5.6%, octamer 2.8%, nonamer 1.1%, decamer 0.3%) FIG. 3(C); analysis was undertaken using a 100Diol-5 Develosil™ HPLC column (Nomura Chemical Co. Ltd, Japan) as for GS-OPC.

Figure 2:
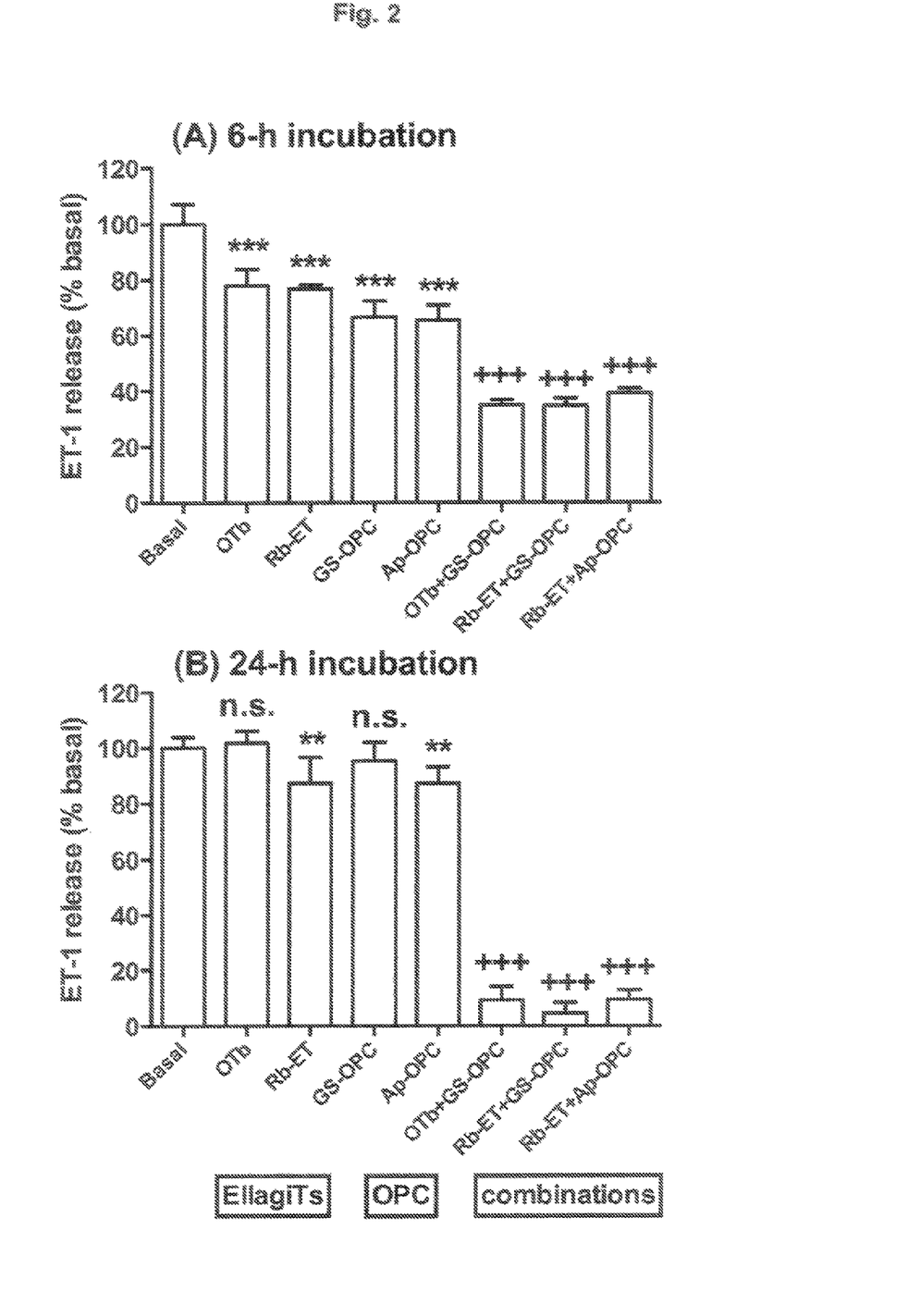
FIG. 2: Effect of oenothein B, raspberry seed ellagitannin extract, procyanidins and mixtures thereof on endothelin-1, a vasoconstrictor and biomarker associated with endothelial dysfunction.

Ellagitannins: oenothein B (OTb, 1 µg/ml), raspberry seed extract (Rb-ET 2 µg/ml); oligomeric procyanidins (OPC): grape seed extract (GS-OPC, 1 µg/ml) and apple extract (Ap-OPC, 1 µg/ml) purified as above, were incubated either alone, or in combination, with bovine aortic endothelial cells for 6 h and 24 h (FIGS. 2(A) and 2(B)). After the respective incubation periods, conditioned media samples were collected for assay of endothelin-1 (see *Journal of Agricultural and Food Chemistry*, 2010, 58: 4008-13). Data (mean±SD) are shown as a percentage of the corresponding basal values at 6 h or 24 h. Statistical differences were determined by ANOVA (=P<0.01; *=P<0.001 indicates significant difference compared to basal values; +++=P<0.001 compared to the individual components of the combinations alone).

While the ellagitannins (oenothein B, raspberry seed extract) and oligomeric procyanidins (grape seed extract, GS-OPC, and apple extract, Ap-OPC) alone all inhibited endothelin-1 synthesis over 6 h the combinations had a greater effect than the extracts used separately (FIG. 2(A)). However, after 24 h the effects of the extracts alone were much reduced with only raspberry seed extract and apple extract causing a significant reduction. In comparison the combinations of ellagitannins and procyanidins caused a remarkably sustained and increased reduction in endothelin-1 synthesis (FIG. 2(B)).

These data clearly show that use of an ellagitannin in combination with a procyanidin produces a synergistic effect on endothelial function that has a much greater magnitude of response and longer duration of action than either ellagitannins or procyanidins alone. The consequence of this combination is likely to be greater and longer-lasting reversal of endothelial dysfunction.

Figure 4:
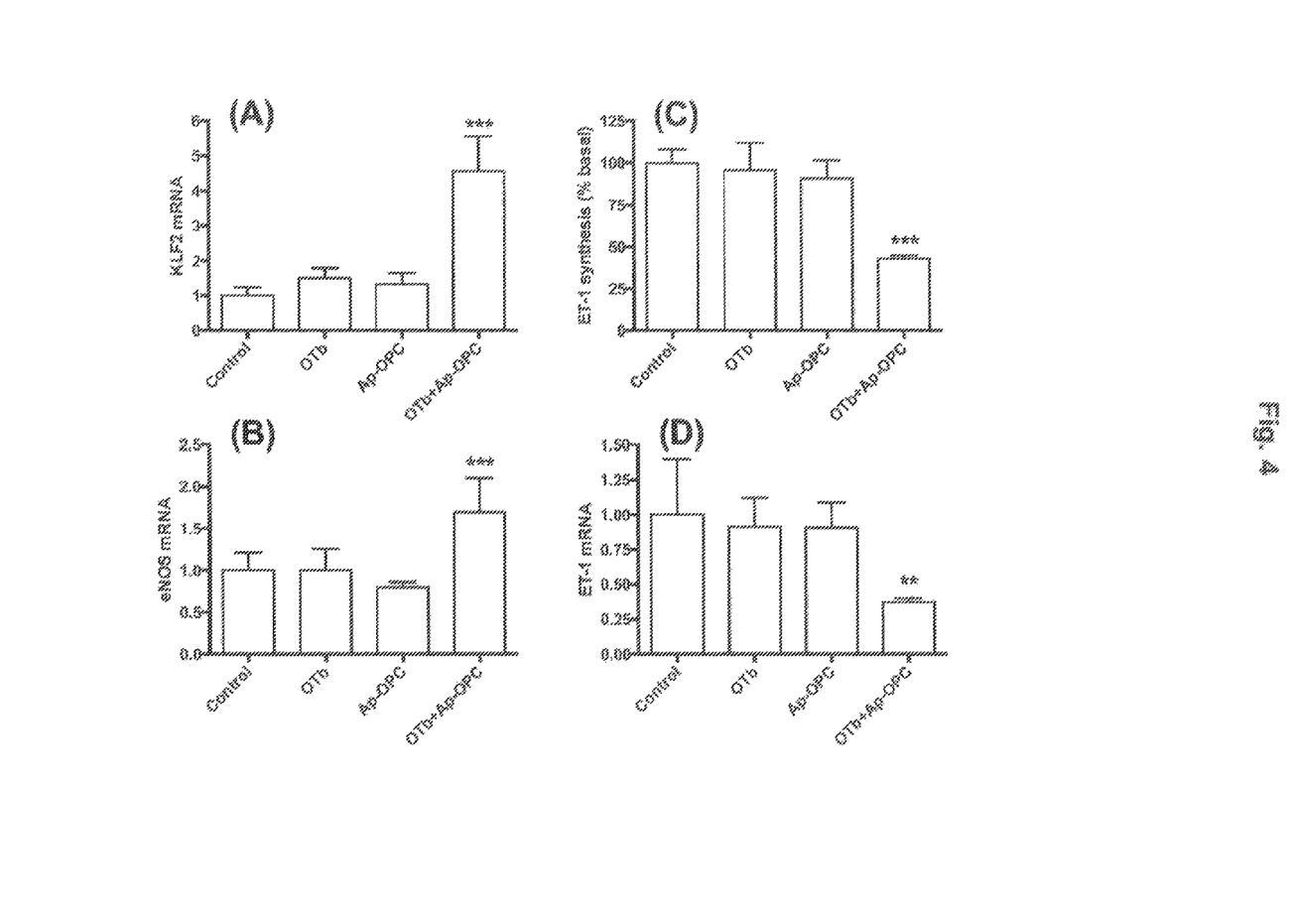
FIG. 4: Effect of oenothein B, procyanidins and mixtures thereof on biomarkers associated with reversal of endothelial dysfunction.

Example 19: Effect of Oenothein B, Procyanidins and Mixtures Thereof on Biomarkers Indicating Reversal of Endothelial Dysfunction Oenothein B (OTb, 1 µg/ml) and apple oligomeric procyanidins (Ap-OPC, 1 µg/ml) purified as above (see EXAMPLE 18), were incubated either alone, or in combination, with bovine aortic endothelial cells for 24 h. After 24 h incubation, conditioned media samples were collected for assay of endothelin-1, and cells were lysed for measurement of relative levels of mRNA for endothelin-1, Kruppel-like factor 2 (KLF2) and endothelial nitric oxide synthase (eNOS) by qRT-PCR (see *Journal of Agricultural and Food Chemistry*, 2010, 58: 4008-13). Levels of mRNAs were normalised to the mRNA levels of the housekeeping gene RNA polymerase 2, and are shown in FIG. 4 as ratios to control levels for the respective mRNAs. Data are shown as mean±SD. Statistical differences were determined by ANOVA (=P<0.01; *=P<0.001 indicates significant difference between the effects of OTB and OPC in combination compared to control values, oenothein B alone and apple OPC alone).

While use of either oenothein B or apple OPC alone for 24 h has some effect on KLF2 mRNA levels, the effects are relatively insignificant (see FIG. 4(A)). However, when oenothein B is used in combination with apple OPC, the increase in KLF2 mRNA levels is remarkable, and is indicative of a synergistic interaction between the ellagitannin and procyanidin. Similar results are found on other biomarkers of endothelial function. Thus, use of either oenothein B or apple OPC has little effect on eNOS mRNA levels after 24 h (see FIG. 4(B)). However, when oenothein B and apple OPC are used in combination, a significant increase in eNOS expression is observed. Turning to FIGS. 4(C) and 4(D), endothelin-1 (ET-1) mRNA and endothelin-1 total synthesis is largely unaffected by use of either oenothein B or apple OPC alone for 24 h, while use of oenothein B in combination with apple OPC results in a marked decrease in endothelin-1 mRNA levels and total endothelin-1 synthesis.

These data clearly show that use of an ellagitannin in combination with a procyanidin/proanthocyanidin can produce a synergistic effect on functional biomarkers that indicate reversal of endothelial dysfunction.

The invention claimed is:

1. A method of preventing, delaying the onset of, or treating endothelial dysfunction comprising administering to a patient suffering from or at risk of developing endothelial dysfunction, either simultaneously or sequentially, oenothein B in combination with at least one proanthocyanidin, wherein said oenothein B and proanthocyanidin are administered in therapeutically effective amounts.

2. The method of claim 1, further comprising administering aspartic acid or an aspartate to the patient, aspartic acid or aspartate is administered in therapeutically effective amount, and wherein the aspartic acid or aspartate is administered either simultaneously or sequentially with the oenothein B and/or at least one proanthocyanidin.

3. The method of claim 1, further comprising administering to a patient citrulline or a citrulline salt, and aspartic acid or an aspartate, wherein said citrulline or citrulline salt, and aspartic acid or aspartate are administered in therapeutically effective amounts, and wherein the citrulline or citrulline salt and aspartic acid or aspartate is administered either simultaneously or sequentially with the oenothein B and/or with the at least one proanthocyanidin.

4. The method of claim 1, wherein the at least one proanthocyanidin is at least one procyanidin.

5. The method of claim 4, wherein the at least one proanthocyanidin is a mixture comprising procyanidins selected from the group consisting of procyanidin trimers, procyanidin tetramers, procyanidin pentamers and/or procyanidin hexamers.

6. The method of any one of claims 1, 2, 3, and 4, wherein the endothelial dysfunction is in the form of one or more diseases selected from arteriosclerosis, hypertension, pulmonary hypertension, coronary artery disease, chronic heart failure, peripheral artery disease, diabetes, chronic renal failure and erectile dysfunction.

7. The method of claim 1, wherein the proanthocyanidin has a molecular weight of about 800 to about 1900 Daltons.

8. The method of claim 1, wherein said proanthocyanidin is obtained from apple, cocoa bean, cranberry, grape seed, hawthorn, maritime pine bark or sorghum.

9. The method of claim 8, wherein said proanthocyanidin is derived from grape seeds and is a galloylated procyanidin.

10. The method of claim 1, wherein oenothein B is obtained from pomegranate fruits.

11. The method of claim 1, wherein oenothein B is obtained from any plant in the *Epilobium* genus.

12. The method of claim 11, wherein said plant is *Epilobium parviflorum* (smallflower hairy willowherb).

13. The method of claim 1, wherein the weight ratio of oenothein B to the at least one proanthocyanidin is in the range of about 10:1 to about 1:10.

* * * * *